United States Patent
LaCourse et al.

(10) Patent No.: US 7,028,562 B2
(45) Date of Patent: Apr. 18, 2006

(54) VACUUM MEMBRANE EXTRACTION SYSTEM

(75) Inventors: William R. LaCourse, Catonsville, MD (US); Patrick Devin Wigington, Fair Haven, NJ (US)

(73) Assignee: University of Maryland, Baltimore County, Baltimore, MD (US)

( * ) Notice: Subject to any disclaimer, the term of this patent is extended or adjusted under 35 U.S.C. 154(b) by 0 days.

(21) Appl. No.: 10/772,470

(22) Filed: Feb. 6, 2004

(65) Prior Publication Data

US 2004/0154414 A1    Aug. 12, 2004

Related U.S. Application Data

(60) Provisional application No. 60/445,357, filed on Feb. 6, 2003.

(51) Int. Cl.
*G01N 1/00* (2006.01)

(52) U.S. Cl. .................................... 73/863.23

(58) Field of Classification Search ............... 73/19.02, 73/19.09, 19.1, 19.12, 23.41, 23.42, 863.11, 73/863.12, 863.23, 863.71, 863.72, 864.34, 73/864.81, 864.73, 864.74
See application file for complete search history.

(56) References Cited

U.S. PATENT DOCUMENTS

| | | | |
|---|---|---|---|
| 2,386,832 A * | 10/1945 | Zaikowsky | 73/863.11 |
| 3,111,849 A * | 11/1963 | Broerman | 73/863.71 |
| 3,666,107 A * | 5/1972 | Boggs et al. | 210/238 |
| 3,685,345 A | 8/1972 | Wise | |
| 3,735,558 A * | 5/1973 | Skarstrom et al. | 95/51 |
| 3,976,450 A * | 8/1976 | Marcote et al. | 96/12 |
| 4,426,285 A * | 1/1984 | Davis | 210/109 |
| 4,517,135 A * | 5/1985 | Szerenyi et al. | 261/104 |
| 4,653,998 A * | 3/1987 | Sohma et al. | 431/79 |
| 4,853,013 A * | 8/1989 | Rio et al. | 96/6 |
| 5,035,149 A | 7/1991 | Wierenga | |
| 5,054,328 A * | 10/1991 | Long et al. | 73/864.81 |
| 5,062,708 A * | 11/1991 | Liang et al. | 356/316 |
| 5,297,432 A * | 3/1994 | Traina et al. | 73/864.34 |
| 5,411,087 A * | 5/1995 | Taylor | 166/264 |
| 5,458,010 A * | 10/1995 | Traina et al. | 73/864.12 |
| 5,502,308 A * | 3/1996 | Wong | 250/338.5 |
| 5,639,956 A | 6/1997 | Christy | |

(Continued)

OTHER PUBLICATIONS

Columbia Technologies Membrane Interface Probe (MIP) Facts, available at: http://www.columbiadata.com/mip/mi-p.cfm?, accessed Jan. 23, 2004.

(Continued)

*Primary Examiner*—Robert Raevis
(74) *Attorney, Agent, or Firm*—Sterne, Kessler, Goldstein & Fox PLLC

(57) ABSTRACT

The present invention relates to apparatus for sampling and analysis of gas phase molecules. A source of negative pressure is used to draw gas phase molecules through a gas-permeable membrane. The gas phase molecules are then directed into an analyzer, suitably a gas chromatograph. The present invention also relates to methods of sampling and analyzing gas phase molecules above and below liquid and soil surfaces

13 Claims, 4 Drawing Sheets

U.S. PATENT DOCUMENTS

| | | | |
|---|---|---|---|
| 5,741,984 A * | 4/1998 | Danylewych-May et al. | 73/864.71 |
| 5,887,491 A * | 3/1999 | Monson et al. | 73/864.74 |
| 6,022,510 A * | 2/2000 | Springmann | 422/101 |
| 6,357,858 B1 * | 3/2002 | Kishima et al. | 347/47 |
| 6,487,920 B1 * | 12/2002 | Robbat, Jr. | 73/863.12 |
| 6,609,434 B1 * | 8/2003 | Hubbell et al. | 73/864.51 |
| 6,649,129 B1 * | 11/2003 | Neal | 422/89 |
| 6,736,883 B1 * | 5/2004 | Sjostrom et al. | 96/112 |
| 6,773,493 B1 * | 8/2004 | Lindstrom | 96/413 |
| 6,776,604 B1 * | 8/2004 | Chobotov et al. | 425/522 |

OTHER PUBLICATIONS

Costanza, J., et al., "Effect of Temperature and Pressure on the MIP Sample Collection Process," Remediation of Chlorinated and Recalcitrant Compounds—2002, Proceedings of the Third International Conference on Remediation of Chlorinated and Recalcitrant Compounds (Monterey, CA; May 20-23, 2002).

* cited by examiner

VACUUM MEMBRANE EXTRACTION SYSTEM

BACKGROUND OF THE INVENTION

1. Field of the Invention

The present invention relates to apparatus for sampling and analysis of gas phase molecules. A source of negative pressure is used to draw gas phase molecules through a gas-permeable membrane. The gas phase molecules are then directed into an analyzer, suitably a gas chromatograph. The present invention also relates to methods of sampling and analyzing gas phase molecules above and below liquid and soil surfaces

2. Background of the Invention

Surface and subsurface analysis of gas phase molecules in soil and liquid sample sites has traditionally been performed by removing a sample from various levels within a site, and then analyzing it at a later time. In the case of soil or ground water sampling, a special probe is positioned on the lower end of a probe rod string and driven into the ground to the particular level at which a sample is to be taken. Thereafter, the soil sample or ground water sample is removed from the probe and analyzed using various detection and quantifying instruments. As is apparent, if it is desirable to investigate a site to determine the presence and/or quantity of certain compounds or contaminants at a variety of different levels, the use of this direct soil/ground water sampling operation can involve a substantial amount of labor and time. More specifically, to detect compounds or contaminants at various levels the probe rod string must be driven to each particular level, a sample taken, and thereafter the sample removed from the ground by removing the probe rod string. Thus, numerous iterations of driving the probe rod string into the ground and then retracting the probe rod string from the ground are required to sample at the various levels.

U.S. Pat. No. 5,035,149 to Wierenga discloses a soil sampling device called a suction lysimeter. In such a device, a receptacle is implanted in the earth with an air conduit extending from the earth's surface into the receptacle. By drawing a vacuum on the air conduit, soil solution is drawn in from the surrounding soil through the porous walls and collected in the receptacle. A separate conduit for transferring the soil solution sample brings the sample to the surface when positive air pressure is applied to the receptacle through the air conduit. Alternatively, transfer to the surface may be effected by vacuum if from a relatively shallow sampler, although this is said to be less desirable because of the danger of volatilizing components of the sample. The sample is then analyzed for volatile gas phase molecules and other solutes at the surface.

U.S. Pat. No. 5,639,956 to Christy, describes a probe capable of detecting and quantifying chemical compounds and contaminants, particularly volatile compounds which either exist wholly in the gas phase at normal soil temperatures, or exhibit a substantial vapor pressure while existing in the soil in the dissolved, liquid, or solid phases. The '956 patent discloses a permeable membrane soil probe consisting of a gas-permeable membrane having an outer surface in contact with a sample site, and an inner surface in fluid contact with a carrier gas that transports gas phase molecules that have diffused through the membrane to a detector device.

The probe disclosed in the '956 patent, however, is diffusion limited. The amount of volatile gas that diffuses through the gas-permeable membrane and into the carrier gas may be minimal, as positive pressure of the carrier gas relative to the sample site is said to limit the amount of sample gas that can diffuse through the membrane. Therefore, there exists a need for a device that can sample volatile gas phase molecules, at surfaces, as well as below soil and liquid surfaces, without the problems associated with using a high pressure carrier gas.

The present invention fulfills this need by providing a membrane extraction system coupled to a vacuum source to facilitate the sampling of gas phase molecules from a sample and transport them to an analyzer.

SUMMARY OF THE INVENTION

In one embodiment, the present invention provides an apparatus for sampling gas phase molecules, comprising: (a) a semi-permeable membrane having a permeate side and a sample side; (b) a support structure that supports the semi-permeable membrane; (c) a vacuum source that generates a reduced pressure at the permeate side of the semi-permeable membrane; and (d) an analyzer in fluid communication with the permeate side of the semi-permeable membrane. In suitable embodiments, the apparatus further comprises a heater for heating the semi-permeable membrane. In other suitable embodiments, the semi-permeable membrane is a gas-permeable tetrafluoroethylene polymer membrane. Suitably, the analyzer is a gas chromatograph. The apparatus may also comprise a trap for collection of condensation, and a sample loop. Suitably, the vacuum source is a vacuum pump.

In another embodiment, the present invention provides for an apparatus for sampling gas phase molecules, comprising: (a) a gas-permeable membrane having a permeate side and a sample side; (b) a support structure that supports the gas-permeable membrane; (c) a heater for heating the gas-permeable membrane; (d) a vacuum pump that generates a reduced pressure at the permeate side of the gas-permeable membrane; (e) a sample loop in fluid communication with the permeate side of the gas-permeable membrane; and (f) a gas chromatograph in fluid communication with the sample loop. In certain such embodiments, the gas-permeable membrane may be a tetrafluoroethylene polymer membrane. In suitable such embodiments, the apparatus may further comprise a trap for collection of condensation.

The present invention also provides for methods for sampling gas phase molecules of a sample, comprising: (a) placing a semi-permeable membrane having a permeate side and a sample side in fluid communication with the sample; (b) generating a reduced pressure on the permeate side of the semi-permeable membrane with a vacuum source to draw the gas phase molecules from the sample through the semi-permeable membrane to the permeate side; and (c) analyzing the gas phase molecules in an analyzer that is in fluid communication with the permeate side of the semi-permeable membrane. In suitable embodiments, the methods of the present invention may be used to sample gas phase molecules that are below or above a soil surface or below or above the surface of a liquid.

The present invention also provides for methods for sampling gas phase molecules of a sample, comprising: (a) placing a gas-permeable, heated membrane having a permeate side and a sample side in fluid communication with the sample; (b) generating a reduced pressure on the permeate side of the gas-permeable membrane with a vacuum pump to draw the gas phase molecules from the sample through the gas-permeable membrane to the permeate side and then to a sample loop; and (c) analyzing the gas phase molecules in a gas chromatograph that is in fluid communication with the sample loop.

BRIEF DESCRIPTION OF THE FIGURES

The foregoing and other features and advantages of the invention will be apparent from the more particular description of the invention, as illustrated in the accompanying drawings. The drawings are not to scale.

DETAILED DESCRIPTION OF THE INVENTION

Suitable embodiments of the present invention are now described with reference to the figures, where like reference numbers indicate identical or functionally similar elements. While specific configurations and arrangements are discussed, it should be understood that this is done for illustrative purposes only. A person skilled in the relevant art will recognize that other configurations and arrangements can be used without departing from the spirit and scope of the invention.

Figure 1:
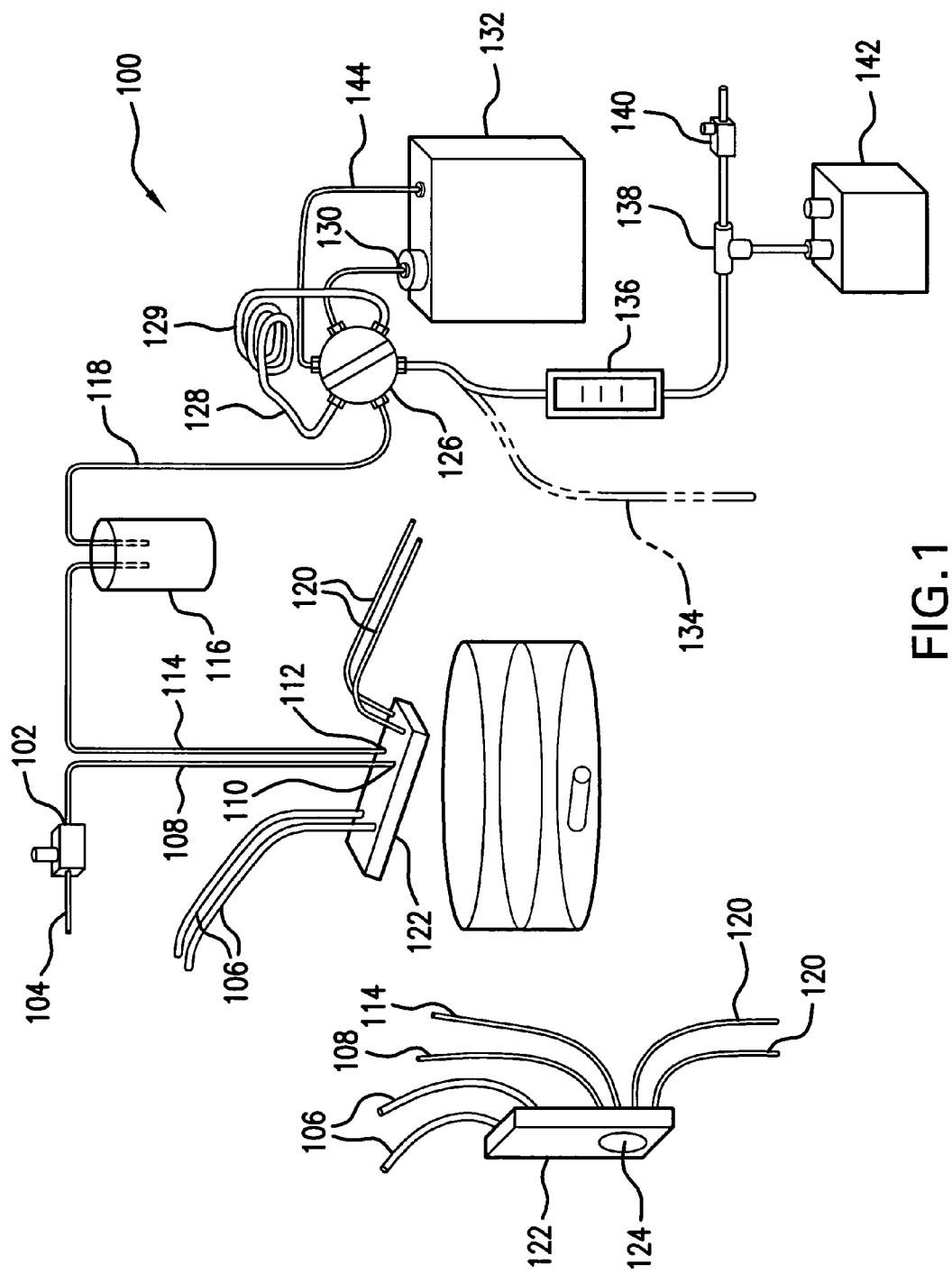
FIG. 1 is a diagram of an embodiment of an apparatus for sampling gas phase molecules in accordance with the present invention.

Referring to FIG. 1, an apparatus for sampling gas phase molecules in accordance with the present invention is shown. Vacuum membrane extraction system 100 comprises a semi-permeable membrane 124 (referred to interchangeably herein as membrane 124) in fluid communication with vacuum source 142. Suitably, semi-permeable membrane 124 is a gas-permeable membrane, which is supported by a support structure, suitably membrane module 122. Membrane module 122 may suitably be connected to a voltage source through wires 106. By supplying a source of electrical current to membrane module 122, temperature of membrane module 122, as well as membrane 124, will increase by resistance heating. As one of ordinary skill in the art will appreciate, other heaters may be used in the practice of the invention. The temperature of membrane module 122 and membrane 124 may be monitored with a thermocouple connected to membrane module 122 through thermocouple wires 120. Suitably, the support structure shown as membrane module 122 is a dismantled membrane/heater block from a Geoprobe® membrane interface probe, disclosed in U.S. Pat. No. 5,639,956, to Christy. Wires 106 are suitably connected to a variable autotransformer in order to control the temperature of membrane module 122 and membrane 124.

Membrane 124 is formed of a circular disc of stainless steel screen which has been coated with a polymer. The formation and materials for creating membrane 124 are disclosed in U.S. Pat. No. 5,639,956. The polymer is applied in a manner well known in the art such that the openings of the screen are filled, thus making the screen impervious to the bulk flow of either gases, liquids or solids. However, the polymer itself is actually porous, and is permeable to the diffusion of certain compounds, suitably gas phase molecules. Tetrafluoroethylene (TFE) polymer manufactured by E.I. Du Pont de Nemours & Co. of Wilmington, Del., is a suitable type of polymer to be used to coat the screen. TFE allows for gas phase molecules to cross membrane 124, but does not allow for bulk flow of water or solids. TFE is baked onto the screen in successive layers, and allows maximum diffusion and minimum sorption of contaminant compounds. However, as indicated above, other polymers could be used which have different permeability attributes. For instance, a polymer could be chosen which will admit polar compounds but exclude nonpolar compounds.

Inlet gas line 108, attached to the inlet gas connection 110 of membrane block 122, may be left open to the atmosphere, or may supply an inert gas, suitably nitrogen or helium gas, to membrane block 122 and membrane 124 from an inert gas source 104 under the control of a flow control valve 102. In suitable embodiments, inert gas may be supplied to membrane block 122 and membrane 124 if purging of inlet 108 or outlet lines 114 or 118 from membrane 124 to analyzer 132 is desired. Outlet gas connection 112 of membrane module 122 is connected to outlet gas line 114 that carries gas phase molecules that are drawn through membrane 124 to analyzer 132. Outlet gas line 114 may further comprise a trap 116 to collect condensation, though in suitable embodiments, outlet gas line 114 is connected directly to, and may be the same as, outlet gas line 118 to analyzer 132. In suitable embodiments, trap 116 may be a capped glass vial, or other reservoir suitable for use as a trap. Outlet gas line 118 to analyzer 132 is connected to a two-position, six-port sampling valve 126. Any suitable tubing material may be used for inlet and outlet gas lines 108, 114 and 118, as well as other tubing connections utilized in the apparatus of the present invention. Suitable tubing materials include, but are not limited to, stainless steel, copper, nylon, PolyEtherEtherKetone (PEEK® from Vitrex), Flourinated Ethylene-Propylene (FEP), Polytetrafluoroethylene (PTFE), Perfluoroalkoxy (PFA), Viton® fluoroelastomer from DuPont, and Ethylene Tetrafluoroethylene (ETFE), TEFZEL® from DuPont.

Membrane 124 has an outer, sample side in contact with the sample, and an inner, permeate side in fluid contact with both inlet gas line 108 and outlet gas line 114. Gas phase molecules are drawn from the sample, through membrane 124, to the permeate side of membrane 124, and into outlet gas line 114. Heating membrane module 122 and membrane 124 helps to heat the sample and thereby increase the volatility of surrounding gas phase molecules. Suitably, membrane module 122 and membrane 124 are heated above the ambient temperature of a sample. Ambient temperature may be the temperature of a surrounding room, or in natural settings, the temperature of the surrounding air, soil sample site, or liquid sample site. In certain such embodiments, membrane module 122 and membrane 124 may be heated to about 40° C. to about 300° C., to about 80° C. to about 200° C., to about 100° C. to 150° C., to about 100° C., to about 105° C., to about 110° C., to about 115° C., to about 120° C., to about 125° C., to about 130° C., to about 135° C., to about 140° C., to about 145° C., or to about 150° C. As used herein, when referring to any numerical value, "about" means a value of ±10% of the stated value (e.g. "about 100° C. encompasses a range of temperatures from 90° C. to 110° C., inclusive). In other embodiments of the present invention, membrane module 122 does not have to be heated, and may be used at ambient temperature to sample gases that are already volatile at the temperature of the surrounding environment.

To sample gas phase molecules, vacuum source 142 is used to generate a reduced pressure at the permeate side of membrane 124. Suitably, vacuum source 142 is a vacuum pump, fitted with a control valve 138 and an inlet for vacuum pump makeup gas 140. Reduced pressure from vacuum source 142 is controlled by control valve 138 to suitably supply a flow rate of about 5 to about 20 ml/min, though other vacuum pressures may be used in accordance with the present invention as may be determined by the ordinarily skilled artisan.

In suitable embodiments, inlet gas line 108 is closed off to both atmospheric and inert gas. In other suitable embodiments, an inert gas source, suitably helium or nitrogen, is used to supply a low level of carrier gas to the inner surface of membrane 124 through inlet gas line 108. The amount of carrier gas is maintained at a low level using flow control valve 102 so as to provide a minimal amount of fluid in order to help prevent outlet gas line 114 from collapsing as a result of the reduced pressure from vacuum source 142. The reduced pressure at the permeate side of membrane 124 draws gas phase molecules at the sample through membrane 124 to the permeate side of membrane 124 and then and into outlet gas line 114. In a suitable embodiment of the present invention, outlet gas line 114 may be connected directly to six port sampling valve 126. In other suitable embodiments of the present invention, outlet gas line 114 may be connected to trap 116 in order to collect moisture that is present with the gas phase molecules before the gas phase molecules enter the analyzer. In such embodiments, when trap 116 is used, outlet gas line 118 to analyzer 132 will carry the gas phase molecules from trap 116 to six port sampling valve 126.

During gas phase particle loading, gas phase molecules that have been drawn through membrane 124 are directed into valve 126, and then into sample loop 129. Suitably, sample loop 129 is a 10 mL loop of tubing selected from the tubing materials described herein, although tubing comprising any liquid volume may be used. Sample loop 129 provides a reservoir where gas phase molecules may be circulated and held prior to analysis. In the loading phase, gas phase molecules flow back into, and then out of, valve 126 to flow meter 136, and vacuum source 142. During loading, carrier gas 144 flows in and then out of valve 126, then to analyzer injection port 130 and into analyzer 132. Any inert gas, suitably helium, may be used as carrier gas 144.

In order to inject the gas phase molecules drawn from the sample into analyzer 132, injection of sample loop 129 contents is made by turning valve 126 to the "inject" position. In this position, carrier gas 144 flows from valve 126, through sample loop 129 and pushes the contents of loop 129 into analyzer injection port 130 and analyzer 132 for analysis. In other suitable embodiments of the present invention, sample loop 129 may not be used, and gas drawn from the sample may be directly injected in to analyzer 132.

While a preferred apparatus of the present invention shown in FIG. 1 comprises a gas chromatograph (GC) as analyzer 132, other analyzers may be used in accordance with the present invention. For instance, the output of valve 126 can be directed to a flame ionization detector which is commonly used for sensing hydrocarbons. Further, other analyzers may also be used in parallel with the flame ionization detector. Such analyzers include carbon dioxide, oxygen, or humidity sensors. Gas phase molecules can also be directed to a mass spectrometry detector or, indeed, any device for the measurement of compounds in the gas phase.

A gas chromatograph is an analyzer that takes a gaseous sample, and separates the sample into individual compounds, allowing the identification and quantification of those compounds. The principal components of a typical gas chromatograph are the following: an injector that moves the gases onto the head of the separation column in a narrow band; a separation column (typically a long, coiled tube) that separates the sample mixture into its individual components as they are swept through the column by an inert carrier gas, the separation being based on differential interactions between the components and an immobilized liquid or solid material within the column; a detector that detects and measures components as they exit the separation column; and a data display.

Typical modern GC instruments are configured with a heated-block "flash evaporator" type injector, a long capillary tube column (e.g., 0.3 mm ID×30 meters long), an oven housing the column to maintain and to change the column's temperature in a predictable and reproducible fashion, a flame ionization detector (or other type of detector), and a computer with dedicated hardware/software to process the data collected. Conventional GC instrumentation can be modified by using different columns (different lengths, different inner diameters, different sorbent phases, and different phase thicknesses); different detectors; and different data management systems.

The present invention also provides for methods for sampling gas phase molecules of a sample, comprising: (a) placing a semi-permeable membrane having a permeate side and a sample side in fluid communication with the sample; (b) generating a reduced pressure on the permeate side of the semi-permeable membrane with a vacuum source to draw the gas phase molecules from the sample through the semi-permeable membrane to the permeate side; and (c) analyzing the gas phase molecules in an analyzer, wherein the analyzer is in fluid communication with the permeate side of the semi-permeable membrane.

The present invention also provides for methods for sampling gas phase molecules of a sample, comprising: (a) placing a gas-permeable, heated membrane having a permeate side and a sample side in fluid communication with the sample; (b) heating the gas-permeable membrane; (c) generating a reduced pressure on the permeate side of the gas-permeable membrane with a vacuum pump to draw the gas phase molecules from the sample through the gas-permeable membrane to the permeate side and then to a sample loop; and (d) analyzing the gas phase molecules in a gas chromatograph, wherein the gas chromatograph is in fluid communication with the sample loop.

While in suitable embodiments of the present invention, gas-permeable membrane 124 and membrane module 122 are heated above ambient temperature to increase the volatility of gases at the sample site, the methods of the present invention may be performed without heating the membrane. In certain such embodiments, the methods of the present invention may be used to sample gases that are already volatile at the temperature of the surrounding environment.

The methods and apparatus of the present invention may be used to sample gas phase molecules from any desired sample. Suitably, this sample may be at the earth's surface, or in other embodiments may be below the soil surface. The membrane 124 and membrane module 122 of the present invention may be placed just above a soil surface, directly in contact with the surface, or may be placed below the surface of the soil to sample gas phase molecules. In such embodiments where membrane module 122 is placed below the surface of the soil, membrane 124 will not permit bulk flow of liquids or solids, and therefore only gas-phase molecules at the sample site will be drawn across membrane 124. Heating membrane 124 above ambient temperature will help increase the volatility of gases below the soil surface.

The methods and apparatus of the present invention may also suitably be used to sample gas phase molecules above or below the surface of a liquid. As noted above, membrane 124 does not permit the bulk flow of liquid, and therefore only gas phase molecules will be drawn through to the permeate side of the membrane when membrane module 122 is submerged in a liquid. Heating membrane 124 above ambient temperature will help increase the volatility of gases in the liquid, but care should be taken to not vaporize the primary liquid phase. In the case of liquid water, the temperature of membrane 124 should not be increased above 100° C.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Comparison of Vacuum Membrane Extraction System and Membrane Extraction Using a Sweeping Gas The membrane module used was a dismantled membrane/heater block from a Geoprobe® membrane interface probe. The wiring for the heater was connected to a variable autotransformer (Staco Energy Products Co.) in order to control the temperature. The thermocouple wires were connected to an electronic thermometer (Fisher Scientific) to allow monitoring of the membrane temperature.

The inlet gas line to the membrane module was connected to the regulator of a nitrogen tank by 100'1/16" OD×0.020" ID FEP tubing. The flow control valve was used to ensure either no, or only a small amount of carrier gas, was supplied during the vacuum membrane extraction process. The nitrogen source also provided a sweeping gas if purging of the transfer lines from the membrane to the gas chromatograph (GC) injection valve was needed between analyses. The outlet line used to transfer gas phase molecules to the GC was 1/16" OD×0.020" ID FEP. Lengths of 2' and 100' were used. That tubing was connected to a capped glass vial used as a trap. The trap was connected to the GC injection valve with approximately 1' of 1/16" OD×0.020" ID FEP and 1' of 1/16" stainless steel tubing. The trap was removed from the system during analyses if it was found that the application did not generate condensate in the transfer lines. Fittings used were primarily swagelok (Baltimore Valve and Fitting) with Valco (Valco International) fittings used to connect tubing the GC injection valve.

A two-position, six-port valve sampling and switching valve, model C6WE (Valco International), was used to make injections into the GC. The flow from the membrane was directed into the valve, through a 10 mL sample loop, and out of the valve to a flow meter, trap, and the vacuum pump while the valve was in the "load" position. The carrier gas from the GC flowed in and then out of the valve to the GC injection port in this position. Injection of the sample loop contents was made by turning the valve to the "inject" position. The GC carrier gas then flowed through the sample loop and pushed the contents onto the GC column.

The vacuum pump used was an air/vacuum pressure pump model 400-1903 manufactured by the Bamant Company. Tubing from the system was connected to the vacuum port. A needle valve was attached to the positive pressure port in order to control the vacuum. A tee was also placed in line with the vacuum port to allow a controlled supply of gas with another needle valve.

The GC was a Shimadzu GC 14A equipped with a flame ionization detector (FID). A packed column with 10% OV101, chromasorb-WHF, particle 80/100 10 feet by 1/4" OD, stainless steel was used. Helium carrier gas, as well as air and hydrogen for the FID was purchased from Puritan Medical Products.

Methyl tert-butyl ether, 99% (Acros), was used to prepare a stock standard solution. Working standard solutions were prepared from a 5000 ppm stock MTBE. The solvent was polished reverse osmosis water.

Preparation of the membrane extraction system can occur once the system is assembled and the GC is readied. The vacuum was turned on and controlled so that a flow of approximately 5 to 20 mL/min is pulled. The module was maintained at about 100° C. The GC injection valve was set to the "load" position while sampling. The membrane module was positioned so that it was in contact with the sample site, or in close proximity. Vacuum membrane extraction was performed with the membrane just at the liquid surface, or submerged in an aqueous solution of Methyl tert-butyl ether (MTBE).

Experiments were performed to compare the membrane extraction of the gas-permeable membrane using a vacuum pump and a sweeping gas. In the vacuum mode, the vacuum pump down stream of the membrane and GC injection valve. In sweeping mode, the sweeping gas flows from the nitrogen sweeping gas source to the membrane and then to the GC injection valve.

During the course of the experiments it was observed that no condensate was collected in the trap prior to the GC injection valve. The trap was removed for later experiments using similar experimental conditions.

A first experiment involved the monitoring of a 50 ppm methyl tert-butyl ether (MTBE) in water solution with the membrane just above the surface of the solution. The MTBE solution was maintained at 55° C. with constant stirring. Three modes of operation were compared. The first was a vacuum with a closed inlet so that flow must occur through the membrane only. The nitrogen inlet was opened to the atmosphere in the second setup so that atmospheric air flowed into the tubing and past the permeate side of the membrane. The total flow to the GC injection valve was the sum of that from the membrane and from the inlet tubing. In the third setup, nitrogen at 11.1 mL/min was used as a sweeping gas. The vacuum pump was not used in the third configuration. In all three setups, the temperature of the membrane module was maintained at 112–114° C.

Figure 2:
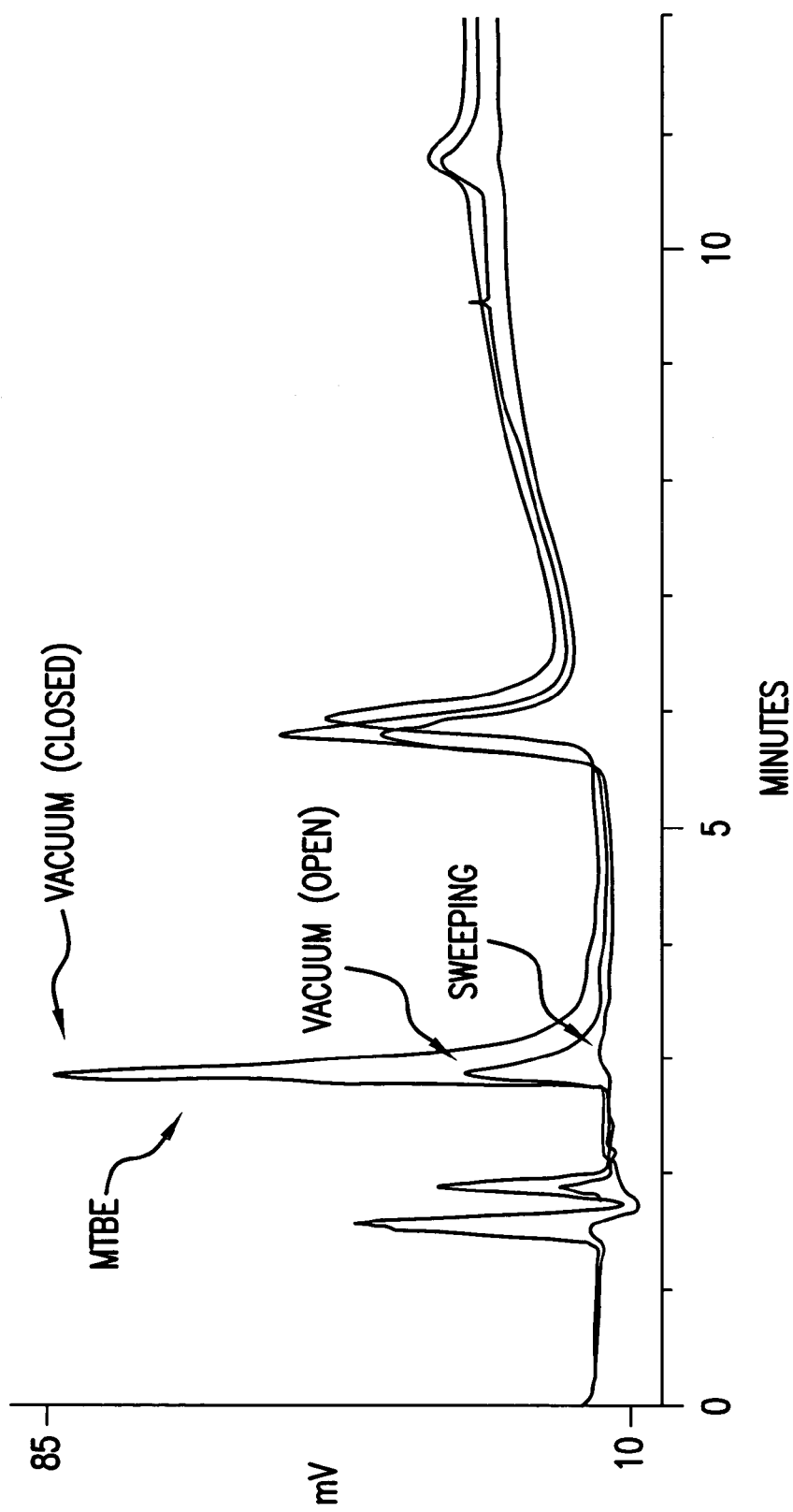
FIG. 2 is a plot showing detection of MTBE comparing, an apparatus comprising a vacuum source for sampling gas phase molecules in accordance with the present invention, with a configuration without a vacuum source.

FIG. 2 shows the detector response from the gas chromatograph as mV vs. time in minutes, comparing all three setups. The peak corresponding to MTBE occurs at approximately 3 minutes for all configurations. The response from the configuration where the vacuum is used alone without the inlet line open to the atmosphere (vacuum (closed)), demonstrated the greatest amount of MTBE sampled and delivered to the GC. When the inlet gas line was opened to the atmosphere (vacuum (open)), the detected amount of MTBE was lower, but still significantly higher than the amount detected when no vacuum was used (sweeping).

Figure 3:
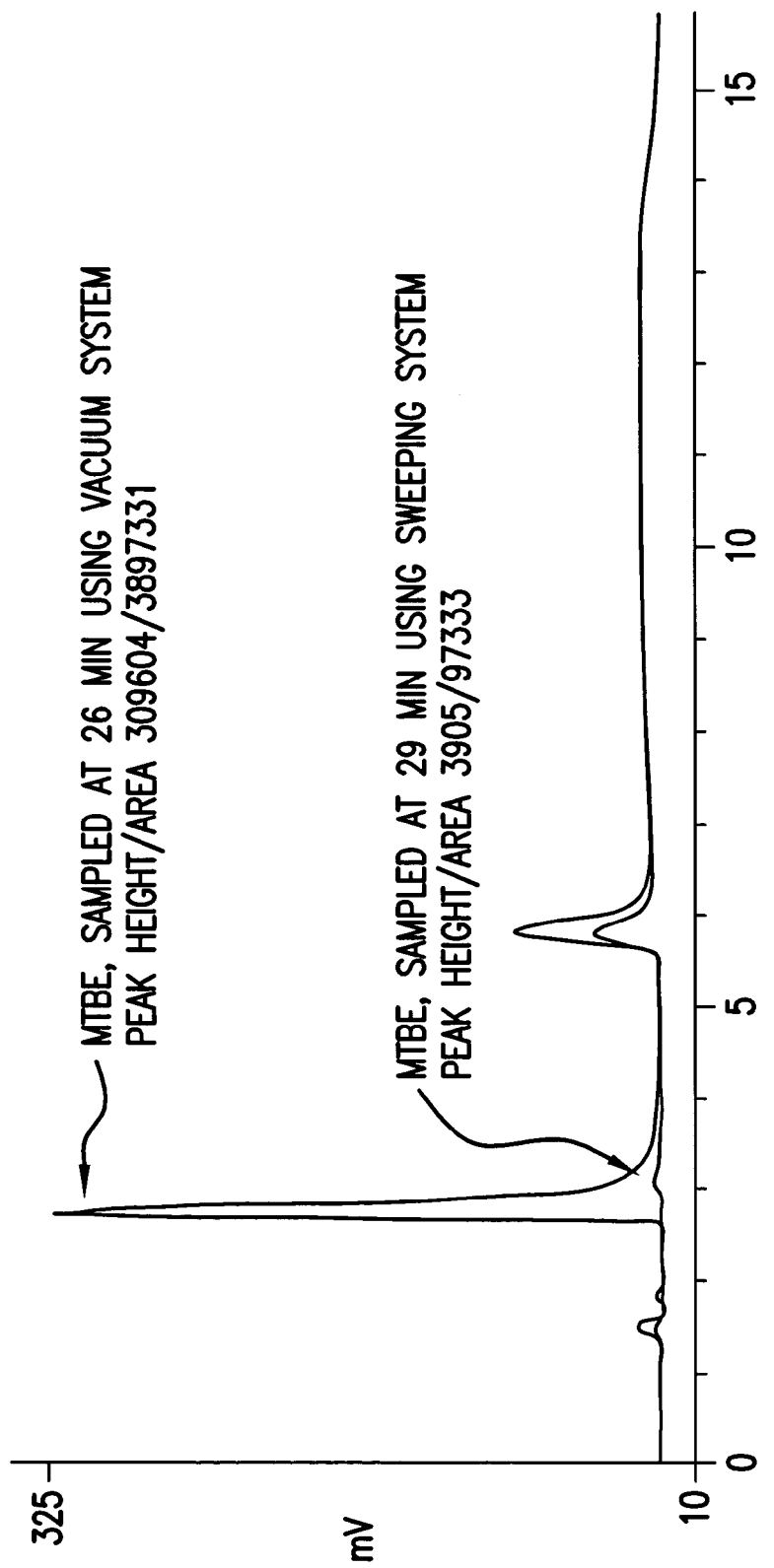
FIG. 3 is a plot showing detection of MTBE comparing, an apparatus comprising a vacuum source for sampling gas phase molecules in accordance with the present invention, with a configuration without a vacuum source.

A second experiment involved the closed inlet vacuum mode and the sweeping mode (i.e. no vacuum source) with the membrane submerged below the surface of a 25 ppm MTBE solution. The MTBE solution was maintained at 50–55° C. and stirred constantly. The membrane module was submerged so that the entire membrane was below the solution surface for the duration of the experiment. The temperature of the membrane module was maintained at about 100° C. via the applied voltage. Inlet and outlet gas transfer lines were 1/16" OD×0.020" ID FEP as noted above. In sweeping mode, a flow of 10 mL/min of nitrogen was supplied through the inlet gas line. A 40 mL trap and sample loop/valve system as described above were used to direct the gas phase sample to the GC for analysis. The relevant parameters of the gas chromatograph are described below:

Injector Temperature: 150° C.
Detector Temperature: 300° C.
Column Temperature: Initial 85° C., hold 4.0 min., 20° C./min to 150° C., hold
Carrier: Helium, 55 mL/min at 85° C.
Flame Ionization Detection
Sample Loop: 10.0 mL, heated to 150° C.
Column: Packed stainless steel, 10'×¼", 10% OV101, chromasorb-WHP), particle 80/100
Noise of system $\leq 0.1$ mV FIG. 3 shows the detector response from the gas chromatograph as mV vs. time in minutes, comparing a vacuum membrane extraction system according to the present invention and a sweeping system, i.e. no vacuum source and only nitrogen passing over the permeate side of the membrane. The MTBE peak noted at about 3 minutes is significantly higher when sampled using a vacuum membrane extraction system according to the present invention compared to the sweeping system.

Figure 4:
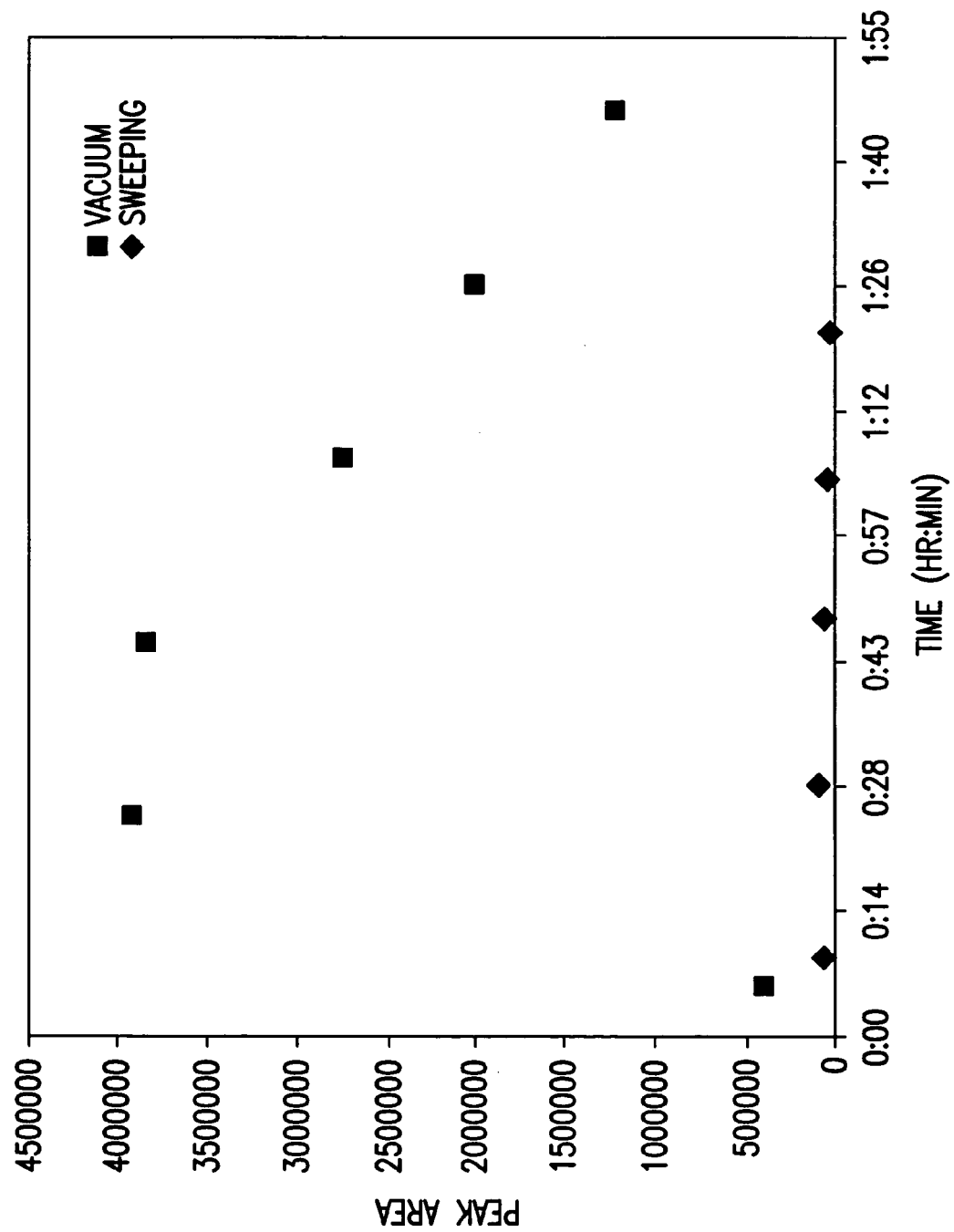
FIG. 4 is a plot showing the peak area of the MTBE detected comparing, an apparatus comprising a vacuum source for sampling gas phase molecules in accordance with the present invention, with a configuration without a vacuum source.

The response from the GC is also represented in FIG. 4 showing the peak area of the MTBE detection for both a vacuum membrane extraction system according to the present invention (vacuum) and a sweeping system (sweeping). The peak area detected is over 700 times greater when using a vacuum membrane extraction system according to the present invention, clearly demonstrating the advantage of the apparatus and methods of the present invention in sampling gas phase molecules.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. An apparatus for sampling gas phase molecules, comprising:
    (a) a semi-permeable, gas-permeable membrane having a permeate side and a sample side;
    (b) a support structure that supports said semi-permeable membrane;
    (c) a heater for said semi-permeable membrane;
    (d) a vacuum source that generates a reduced pressure at said permeate side of said semi-permeable membrane; and
    (e) a gas chromatograph in fluid communication with said permeate side of said semi-permeable membrane,
wherein said semi-permeable membrane does not permit bulk flow of liquids and solids.

2. The apparatus of claim 1, wherein said semi-permeable membrane is a polymer.

3. The apparatus of claim 2, wherein said semi-permeable membrane is a tetrafluoroethylene polymer.

4. The apparatus of claim 1, further comprising a trap in fluid communication with said permeate side of said semi-permeable membrane.

5. The apparatus of claim 1, wherein said vacuum source is a vacuum pump.

6. The apparatus of claim 1, further comprising a sample loop in fluid communication with said permeate side of said semi-permeable membrane and said gas chromatograph.

7. The apparatus of claim 1, wherein said semi-permeable membrane comprises a screen coated with a polymer.

8. The apparatus of claim 7, wherein said screen comprises stainless steel.

9. The apparatus of claim 7, wherein said polymer is a tetrafluoroethylene polymer.

10. A method for sampling gas phase molecules of a sample, comprising:
    (a) placing a semi-permeable, gas-permeable, heated membrane having a permeate side and a sample side in fluid communication with the sample;
    (b) generating a reduced pressure on the permeate side of the semi-permeable membrane with a vacuum pump to draw the gas phase molecules from the sample through the semi-permeable membrane to the permeate side and then to a sample loop; and
    (c) analyzing the gas phase molecules in a gas chromatograph, wherein the gas chromatograph is in fluid communication with the sample loop,
wherein the semi-permeable membrane does not permit bulk flow of liquids and solids.

11. The method of claim 10, wherein the semi-permeable membrane comprises a screen coated with a polymer.

12. The method of claim 11, wherein the screen comprises stainless steel.

13. The method of claim 11, wherein the polymer is a tetrafluoroethylene polymer.

* * * * *